United States Patent [19]

Roy et al.

[11] 4,040,787

[45] Aug. 9, 1977

[54] UREA DETERMINATION OF BIOLOGICAL FLUIDS USING DIACETYLMONOXIME REACTION

[75] Inventors: Alejo V. Roy, Carmel; Jane R. Heiwig, Indianapolis, both of Ind.

[73] Assignee: The Dow Chemical Company, Midland, Mich.

[21] Appl. No.: 678,811

[22] Filed: Apr. 21, 1976

[51] Int. Cl.$^2$ .................. C09K 3/00; G01N 31/06; G01N 33/16
[52] U.S. Cl. .................................. 23/230 B; 252/408
[58] Field of Search ........................ 23/230 B; 252/408

[56] References Cited

U.S. PATENT DOCUMENTS 3,567,374   3/1971   Wybenga ........................ 23/230 B

OTHER PUBLICATIONS

Ceriotti et al., Clin. Chem. Acta, 8, 295-299, (1963).
Ceriotti et al., Clin. Chem. Acta, 11, 519-522, (June, 1965).

*Primary Examiner*—Joseph Scovronek
*Attorney, Agent, or Firm*—James W. Ambrosius

[57]    ABSTRACT

A unique composition and method for the determination of urea using diacetylmonoxime and thiosemicarbazide in an aqueous strong acid to which has been added a color-intensifying amount of a cation selected from the group consisting of ferric and ceric; and a linearity-enhancing amount of 4-amino-antipyrine.

9 Claims, No Drawings

UREA DETERMINATION OF BIOLOGICAL FLUIDS USING DIACETYLMONOXIME REACTION

BACKGROUND OF THE INVENTION

Numerous reagents have been employed in methods for the determination of urea or urea nitrogen in biological fluids such as serum, plasma, urine, or the like. A widely accepted specific method involves incubation of the fluid with urease to bring about the enzymatic release of ammonia, which is then determined quantitatively by nesslerization. The urease nesslerization technique is time consuming and there is a need for more rapid methods. Several rapid methods are in use in which the amount of urea or urea nitrogen in a sample of biological fluid is determined by contacting the biological fluid with a reagent which combines with urea in the biological fluid to form a colored reaction product or chromophor; the depth or intensity of the color produced being proportional to the amount of urea present in the sample of biological fluid. The concentration of urea nitrogen in the sample is then determined by measuring the depth or intensity of the color, usually with a colorimeter or a spectro-photometer. By use of conversion charts or comparisons to standard solutions, the measurement of the color produced by the use of the reagent can be converted to give the concentration of urea nitrogen in the sample.

The diacetylmonoxime reaction has been used for the determination of urea since 1939. See Fearon, *Biochem J.* 33, 902 (1939). When urea is heated with diacetylmonoxime in the presence of a strong acid such as sulfuric, phosphoric, hydrochloric, or nitric a chromophor is formed having an absorption peak at 480 nm. See Natelson, et al., *Am. J. Clin. Path.* 21, 275 (1951); LeMar, et al., *Analytical Chem.* 29, 1233 (1957); Veniamin, et al., *Clin. Chem.* 16, 3 (1970); Lugosi, et al., *Clin. Biochem.* 5, 171 (1972); and Kitamura, *Clin. Chem. Acta* 4, 701 (1959). However, the color developed did not give a linear relationship between urea nitrogen concentration and absorbances. Coulombe and Faureau, *Clin. Chem.* 9, 102 (1963), introduced the use of thiosemicarbazide in conjunction with diacetylmonoxime for serum urea nitrogen determination. The sensitivity of the method was increased, but a different chromophor was produced which had an absorption peak at approximately 535 nm. This reaction required a long heating time (20 minutes or longer), a strong acid media (20% or higher), and the use of a protein-free serum filtrate. At approximately the same time the use of antipyrine was introduced in conjunction with diacetylmonoxime in a strong acid media for the determination of serum urea nitrogen. Ceriotti, et al., *Clin. Chem. Acta* 8, 295 (1963). This increased method sensitivity and produced a linear relationship between the urea nitrogen concentration and the absorbance readings. However, the procedure and its subsequent modifications, produced a third chromophor having a color peak at 460 nm.

The reaction between urea and reagents containing diacetylmonoxime and thiosemicarbazide has had numerous modifications. Marsh, et al., *Clin. Chem.* 11, 624 (1965), incorporated ferric ion into the reagent to intensify the color produced at about 535 nm and at the same time to allow a decrease in the acid concentration. The effect of metallic ions on the urea-diacetylmonoxime-phenazone reaction was described in Ceriotti, et al., *Clin. Chem Acta* 11, 519 (1965). Wybenga et al., *Clin. Chem.* 17, 891 (1971), stabilized the color by adding cadmium sulfate to the reaction mixture. However, all the diacetylmonoxime-thiosemicarbazide methods for urea nitrogen determination show deviation of linearity when the optical density of the color developed approaches a value of about 0.4–0.5 absorbance units.

An additional reference of interest is U.S. Pat. No. 3,567,374.

SUMMARY OF THE INVENTION

The present invention relates to a novel diacetylmonoxime-thiosemicarbazide reagent system which produces a linear relationship between urea nitrogen concentration and color development up to an optical density of about 1.5–1.6 absorbance units when used to determine urea or urea nitrogen concentration in a biological fluid such as serum, plasma, urine or the like. This is accomplished by incorporating a small amount of 4-aminoantipyrine into the reagent system. It has also been found that problems of turbidity and high reagent blank readings are minimized by replacing the ferric ion by the ceric ion.

The 4-aminoantipyrine is the compound responsible for linearizing the relationship between urea nitrogen concentration and absorbances. If this compound is eliminated from the assay system while keeping all other constituents at the same concentrations a non-linear relationship between urea nitrogen concentration and absorbances is obtained. Although 4-aminoantipyrine has been used in conjunction with diacetylmonoxime for the determination of urea nitrogen, the present system is unique because of the combination of thiosemicarbazide and 4-aminoantipyrine in the presence of diacetylmonoxime, and a strong acid. Although not essential, a metal ion such as ferric or ceric can be added to the system to increase the speed and intensity of the color development. This novel combination makes possible a very sensitive method showing excellent linearity between urea nitrogen concentration and absorbance values.

As already discussed the 4-aminoantipyrine is responsible for the linearity of the system that is the subject of the present invention. The thiosemicarbazide is responsible for the system sensitivity. The sensitivity of the system is drastically reduced if thiosemicarbazide is eliminated from the system. Even if the concentration of the 4-aminoantipyrine is increased several fold the sensitivity remains poor. In addition, the faint color developed has an absorption peak at 480 nm indicating a different chromophor is being formed.

DETAILED DESCRIPTION OF THE INVENTION

In the preparation of the materials for admixture with a biological fluid, it is preferred to employ two separate compositions, a first diacetylmonoxime reagent composition and a second reagent composition comprising an analytically-acceptable strong acid, the thiosemicarbazide, the 4-aminoantipyrine, and the salt of a cation selected from the group consisting of ferric and ceric. When the ingredients are thus prepared as two separate compositions, both such compositions are stable for long periods of time prior to use. The separate compositions can be mixed together with urea or a biological fluid in any order or fashion to produce the color employed in the measurement of urea concentration.

The term "analytically-acceptable strong acid" is employed herein to mean those organic and inorganic acids having an ionization constant greater than about 0.001 and which are not detrimentally reactive with urea or the reactants employed or with the chromophor to be produced. The acid employed can be a strong mineral acid such as sulfuric acid, phosphoric acid, hydrochloric acid or a strong organic acid such as trichloroacetic acid, dichloroacetic acid or mixtures thereof. Preferred analytically acceptable strong acids are mixtures of concentrated sulfuric acid and concentrated phosphoric acid containing on a molar equivalent basis from about 40 to 80 molar equivalents of sulfuric acid per 100 molar equivalents of the total acid mixture. The acid mixture of choice contains on a molar equivalent basis from about 55 to about 65 molar equivalents of sulfuric acid and from about 45 to about 35 molar equivalents of phosphoric acid.

As in any quantitative procedure employing diacetylmonoxime as the reagent, sufficient diacetylmonoxime must be employed to produce a measurable color with urea and to combine with all the urea present in the ultimate mixture to form the colored product, thus providing an intensity of color proportional to the amount of urea. The ultimate mixture of reagent and biological fluid preferably contains excess diacetylmonoxime. Similarly, the thiosemicarbazide must be employed in an amount sufficient to intensify the color produced. The amount employed should provide a concentration of thiosemicarbazide in the composition which produces a measurable increase in color intensity and a detectable change in color from yellow to red in the diacetylmonoxime color reaction with urea.

The ferric or ceric ion can be supplied in any convenient form to provide a solution thereof in water. Generally an acid soluble salt of the desired cation is employed. The cation increases the speed and intensity of color development and therefore a color intensifying amount of the cation must be supplied. As noted above, the ceric ion is preferred since it is more soluble than the ferric ion and shows less propensity to precipitate. In particular, the ceric ion accelerates the reaction and increases the sensitivity of the system.

Likewise in the improved reagent and method of the present invention a linearity enhancing amount of 4-aminoantipyrine is required. In the present specification and claims the phrase "linearity enhancing amount" is employed to designate that concentration of 4-aminoantipyrine in the reagent composition that produces a measurable color with diacetylmonoxime and a substantial improvement in linearity. In particular applications, whether or not the amount of 4-aminoantipyrine employed in the reagent is sufficient to provide an intensity of color proportional to the amount of urea in the sample can be determined by the simple expedient of measuring the intensity of color produced with varying known amounts of added 4-aminoantipyrine in the reagent when samples having known urea concentrations are employed.

In the quantitative determination of urea by the method of the invention, the first and second reagent compositions are mixed with the sample, generally a biological fluid or a urea containing substance such as a standard solution. In quantitative operations, the reagents are mixed with a minor amount of a biological fluid containing urea. The biological fluid can be an extract, as from a tissue homogenate or the like, or it can be an animal body fluid such as blood, plasma, serum, urine, lymphatic fluid, bile, cerebrospinal fluids or the like. The biological fluid can be employed directly as a sample or it can be treated by conventional procedures such as dilution, centrifugation, extraction or the like.

In carrying out the reaction the biological fluid is mixed in any order of addition with the first and second reagents in the following proportions — 1 part by volume of biological fluid to about 10–50 parts by volume of diacetylmonoxime reagent and about 50–300 parts by volume of acid reagent. The reagents and sample can be mixed in receptacles of a particular predetermined optical density or absorbance such as the tubes or cuvets conventionally employed with colorimeters or spectrophotometers, if desired. The reagents and the urea in the sample combine at elevated temperatures to form a stable colored product with an intensity of color proportional to the amount of urea. Accordingly, for rapid quantitative results, the mixture should be heated to a temperature of from about 85° to about 115° C within about five to fifteen minutes after mixing. The mixture should then be cooled to a temperature below the stated range. The exact temperature and time for heating are not critical when only qualitative determinations are desired. However, the quantitative accuracy of the method of the invention is greatly enhanced by controlling the heating time and temperature.

Substantial over-heating of the mixture can partially destroy the colored product and impair the accuracy of quantitative results. Thus, for exact quantitative procedures, the mixture should be heated to a given temperature of between about 85° and about 115° C within from about one to five minutes after heating is begun, held at such temperature for a controlled period of time not to exceed about 15 minutes and then cooled to a temperature below the above-stated temperature range within about three to about five minutes after heating has ceased.

The heating step can be conveniently carried out by placing tubes containing the mixture of reagents and sample in a conventional tube heating block at a temperature of 100° C for from 5 to 12 minutes. In a convenient procedure for cooling the mixture, the tubes are removed from the heating block and immersed in a cold water bath for from three to eight minutes. Other conventional means for heating and cooling the tubes can be employed such as hot water or oil baths, ice baths and the like.

The color of the mixture can be measured by any means which will give an accurate measurement of the intensity of color. Preferably, a spectrophotometer or a colorimeter is employed. When the method is carried out in a colorimeter tube or spectrophotometer cuvet, the mixture can then be placed in the instrument and its absorbance or transmittance determined. Otherwise, an aliquot portion of the mixture can be placed in such a tube or cuvet and the intensity of color be determined on a colorimeter or spectrophotometer. In such operations, it is preferred to determine the absorbance or percent transmittance of the mixture with light having a wave-length between about 480 millimicrons and 600 millimicrons. The amount of urea present in the sample can then be determined by a comparison of the percent transmittance or absorbance observed for the sample with the measurements obtained when samples containing known amounts of urea are employed, or the conversion charts or tables prepared from such data.

In making the colorimeter or spectrophotometer determinations, it is desirable to employ the readings obtained on the reagent mixture alone and in the absence of any urea from a sample and to thus measure the difference in absorbance (optical density) or percent transmittance between the sample and the pure reagent (reagent blank). Such procedure minimizes the effect of deviations in the amount of the urea reagent employed in successive determinations. Reagent blank determinations are not generally necessary for successive determinations, so long as the diacetyl monoxime reagent and the second reagent composition are the same as those employed for the original reagent blank determination.

It is also desirable to employ a urea standard when employing the procedure of the invention to determine the amount of urea present in a sample of biological fluid. In this procedure, a standard sample is prepared to contain a known amount of urea and this sample is mixed with the reagents in the same predetermined proportions and treated in the identical procedure as the sample of biological fluid containing an unknown amount of urea. The simultaneous use of a urea standard substantially eliminates the effect of procedural deviations. The employment of the standard also permits the calculation of urea concentration in the sample of biological fluid by comparison of the readings obtained with the standard and the sample.

In a convenient procedure, each sample or group of samples to be analyzed, a urea standard sample and a reagent blank composition are treated simultaneously. Additional biological fluid sample tubes can be prepared, so long as all tubes can be heated and cooled at the same temperatures simultaneously. The intensity of color for the urea standard and the sample tubes is then measured, taking account of the reagent blank, and the concentration of urea in the sample is obtained by comparing the intensity of color in the sample tube with the intensity of color produced by the known concentration of urea in the urea standard.

The following examples illustrate the present invention but are not to be construed as a limitation thereon.

EXAMPLE 1

A preferred embodiment of the first and second reagents described above contain the following constituents in the indicated proportions.

| Acid Reagent | |
|---|---|
| Concentrated sulfuric acid | 5.5 ml |
| Concentrated phosphoric acid | 4.6 ml |
| Thiosemicarbazide | 0.012 grams |
| 4-aminoantipyrine | 0.038 grams |
| Ceric ammonium sulfate | 0.0125 grams |
| Distilled water | — |
| | 100 ml total vol. |

Diacetylmonoxime Solution

Each 100 ml of aqueous solution contains 1.2 grams of diacetylmonoxime.

EXAMPLE 2

The recommended procedure for carrying out the determination of urea in a body fluid is as follows:

a. Appropriately mark each of three substrate vials test, blank, and standard.

b. Add 5 ml of the acid reagent shown in Example 1 above to each of the three vials.

c. To the appropriate vial add 0.020 ml of the test sample, urea standard, and water.

d. Add 0.5 ml of the diacetylmonoxime solution to each of the three vials and mix by shaking for approximately 5 seconds.

e. Incubate the vials for 8 minutes at 100° C and then cool for about five minutes on a cold (10°-20° C) water bath.

f. Using a colorimeter or spectrophotometer with a wave length of between 500 to 550 nm (525 nm being preferred) read and record the absorbances of each of the vials, the indicating device on the spectrophotometer or colorimeter having been set previously to read zero absorbance for distilled water.

The concentration of urea in the test sample is calculated according to the following equation:

$$A - B (X)/(C - B)$$

wherein:
A = absorbance of test sample
B = absorbance of reagent blank
C = absorbance of urea standard
X = concentration of urea nitrogen in urea standard in milligrams/100 ml of water

EXAMPLE 3

Using the reagents of Example 1 and the general procedure outlined in Example 2 above a series of standards having from 20 to 100 milligrams of urea nitrogen per 100 mls were tested for absorbance and compared to theoretical linear values for the standard. The results are shown in Table I below.

TABLE I

| Description of Sample Tested | Absorbance Readings* | | |
|---|---|---|---|
| | Against Water | Net Absorbance Std.-Water Blank | Theoretical Linear Values for Std. |
| Water blank | 0.009 | — | — |
| 20 mg urea | 0.297 | 0.288 | 0.288 × 1 = 0.288 |
| 40 mg urea | 0.585 | 0.576 | 0.288 × 2 = 0.576 |
| 60 mg urea | 0.875 | 0.866 | 0.288 × 3 = 0.864 |
| 80 mg urea | 1.167 | 1.158 | 0.288 × 4 = 1.152 |
| 100 mg urea | 1.445 | 1.436 | 0.288 × 5 = 1.440 |

*Absorbance reading made on a DOW$^R$ Enzyme Spectrophotometer set at 525 nm.

It will be noted that excellent correlation is present between the theoretical linear values for the standard and the test values obtained by subtracting the absorbance values for the water blank from the net absorbance of each standard. Thus the linearity and accuracy of the procedure embodiment in the present invention is demonstrated.

I claim:

1. In a reagent composition useful in conjunction with diacetylmonoxime in the determination of urea in a biological fluid, said composition comprising thiosemicarbazide in an aqueous analytically-acceptable strong acid selected from the group consisting of sulfuric acid, phosphoric acid, hydrochloric acid, trichloroacetic acid, dichloroacetic acid and mixtures thereof, the improvement which comprises, as an additional ingredient in said composition, a linearity-enhancing amount of 4-aminoantipyrine, whereby in the presence of urea a chromophor is formed having an absorbance peak between 500 and 550 nanometers.

2. The composition of claim 1 wherein the analytically acceptable strong acid is a mixture of sulfuric acid and phosphoric acid containing from about 55 to 65 molar equivalents of sulfuric acid per 100 molar equivalents of the total acid mixture.

3. The composition of claim 1 further comprising a color intensifying amount of a cation selected from the group consisting of ferric and ceric.

4. The composition of claim 3 wherein the cation is ceric.

5. In a method for the determination of urea nitrogen in biological fluids which comprises mixing a biological fluid with diacetylmonoxime, thiosemicarbazide, and an aqueous solution of an analytically-acceptable strong acid selected from the group consisting of sulfuric acid, phosphoric acid, hydrochloric acid, trichloroacetic acid, dichloroacetic acid and mixtures thereof, and heating the resulting mixture, the improvement which comprises the step of adding a linearity-enhancing amount of 4-aminoantipyrine to the mixture prior to the heating step, whereby a chromophor is formed having an absorbance peak between 500 and 550 nanometers when urea is present.

6. The method of claim 5 further comprising adding a color intensifying amount of a cation selected from the group consisting of ferric and ceric to the mixture.

7. The method of claim 6 wherein the cation is ceric.

8. The method of claim 5 wherein the biological fluid is selected from the group consisting of serum and plasma.

9. The method of claim 8 wherein the biological fluid is serum.